(12) United States Patent
Nam et al.

(10) Patent No.: US 10,390,701 B2
(45) Date of Patent: Aug. 27, 2019

(54) APPARATUS AND METHOD FOR ESTIMATING BIOMETRIC INFORMATION

(71) Applicant: SAMSUNG ELECTRONICS CO., LTD., Suwon-si (KR)

(72) Inventors: Jung Yong Nam, Hwaseong-si (KR); Joon Hyung Lee, Seongnam-si (KR); Ki Young Chang, Yongin-si (KR); Hyeong Seok Jang, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 15/608,535

(22) Filed: May 30, 2017

(65) Prior Publication Data
US 2018/0132718 A1 May 17, 2018

(30) Foreign Application Priority Data
Nov. 17, 2016 (KR) .................. 10-2016-0153165

(51) Int. Cl.
A61B 5/00 (2006.01)
A61B 5/01 (2006.01)
A61B 5/145 (2006.01)
H04B 10/69 (2013.01)
A61B 5/1455 (2006.01)
A61B 5/1495 (2006.01)
G06F 16/435 (2019.01)

(52) U.S. Cl.
CPC .......... A61B 5/0008 (2013.01); A61B 5/0075 (2013.01); A61B 5/01 (2013.01); A61B 5/1455 (2013.01); A61B 5/1495 (2013.01); A61B 5/14532 (2013.01); A61B 5/14546 (2013.01); A61B 5/7203 (2013.01); G06F 16/436 (2019.01); H04B 10/6911 (2013.01)

(58) Field of Classification Search
CPC .............. A61B 5/14532; A61B 5/1455; A61B 5/14533
See application file for complete search history.

(56) References Cited

U.S. PATENT DOCUMENTS

| | | | |
|---|---|---|---|
| 5,028,787 A | 7/1991 | Rosenthal et al. |
| 5,068,536 A | 11/1991 | Rosenthal |
| 5,077,476 A | 12/1991 | Rosenthal |
| 5,086,229 A | 2/1992 | Rosenthal et al. |

(Continued)

FOREIGN PATENT DOCUMENTS

| | | |
|---|---|---|
| JP | 2004226277 A | 8/2004 |
| JP | 20085988 A | 1/2008 |

(Continued)

Primary Examiner — John R Downey
(74) Attorney, Agent, or Firm — Sughrue Mion, PLLC

(57) ABSTRACT

An apparatus configured to estimate biometric information includes a sensor configured to measure a light signal reflected from a subject and a temperature of the subject, and a processor configured to perform temperature correction on the light signal reflected from the subject based on the temperature of the subject using a light signal-temperature relationship between the light signal reflected from the subject and the temperature of the subject to thereby obtain a temperature-corrected light signal, and estimate the biometric information of the subject based on the temperature-corrected light signal.

16 Claims, 8 Drawing Sheets

(56) References Cited

U.S. PATENT DOCUMENTS

| | | | |
|---|---|---|---|
| 5,204,532 A | 4/1993 | Rosenthal | |
| 5,218,207 A | 6/1993 | Rosenthal | |
| 5,237,178 A | 8/1993 | Rosenthal et al. | |
| 5,362,966 A | 11/1994 | Rosenthal et al. | |
| 5,365,066 A | 11/1994 | Krueger, Jr. et al. | |
| 5,436,455 A | 7/1995 | Rosenthal et al. | |
| 5,438,201 A | 8/1995 | Rosenthal et al. | |
| 5,574,283 A | 11/1996 | Quintana | |
| 5,576,544 A | 11/1996 | Rosenthal | |
| 5,876,348 A * | 3/1999 | Sugo | A61B 5/02125 600/485 |
| 6,066,847 A | 5/2000 | Rosenthal | |
| 7,041,468 B2 | 5/2006 | Drucker et al. | |
| 9,603,521 B2 | 3/2017 | Cho et al. | |
| 2005/0043603 A1* | 2/2005 | Ishler | A61B 5/0008 600/365 |
| 2006/0004270 A1* | 1/2006 | Bedard | A61B 5/14532 600/316 |
| 2006/0281982 A1 | 12/2006 | Grata et al. | |
| 2007/0225606 A1* | 9/2007 | Naghavi | A61B 5/015 600/438 |
| 2009/0082680 A1* | 3/2009 | Totterman | A61B 5/0452 600/508 |
| 2009/0105564 A1* | 4/2009 | Tokita | A61B 5/14532 600/310 |
| 2011/0190607 A1* | 8/2011 | Matzinger | G01N 21/8483 600/316 |
| 2016/0015301 A1 | 1/2016 | Elliott et al. | |

FOREIGN PATENT DOCUMENTS

| | | |
|---|---|---|
| JP | 201268263 A | 4/2012 |
| KR | 19937001738 A | 6/1993 |
| KR | 1020080026159 A | 3/2008 |
| KR | 1020090098800 A | 9/2009 |
| KR | 1020160032789 A | 3/2016 |
| WO | 9923479 A1 | 5/1999 |
| WO | 0170330 A3 | 9/2001 |

* cited by examiner

APPARATUS AND METHOD FOR ESTIMATING BIOMETRIC INFORMATION

CROSS-REFERENCE TO RELATED APPLICATION(S)

This application claims priority under 35 USC § 119(a) of Korean Patent Application No. 10-2016-0153165, filed on Nov. 17, 2016, in the Korean Intellectual Property Office, the entire disclosure of which is incorporated herein by reference in its entirety for all purposes.

BACKGROUND

1. Field

Apparatuses and methods consistent with exemplary embodiments relate to the estimation of biometric information of a subject.

2. Description of Related Art

In the past, healthcare services were centered on the treatment of illnesses preliminarily in hospitals and medical institutions. However, with a growing interest in quality of life and well-being as well as an improvement in living standards, there has been an increasing interest in proactive health management services of diseases by the measurement of the health status of healthy people.

In a traditional method of non-invasively measuring a substance in the blood, the concentration of a substance in the blood is measured by a scattered light signal transmitted through the blood being tested. A change in the concentration of a substance in the blood may be represented by a change in a scattering coefficient of the blood. The change in the scattering coefficient may be obtained from a change in the scattered light signal, and thus, the concentration of the substance in the blood may be estimated on the basis of the change in the scattered light signal. In order to accurately estimate the concentration of the substance in the blood from the change in the scattered light signal, the measured change of the scattered light signal should be caused by nothing other than the change in the scattering coefficient of the blood. However, in reality, a change in the temperature of the skin or tissue that is in contact with the sensor also affects the scattered light signal, and thus, it is desirable to correct for this influence, in order to obtain more accurate results.

To this end, a method of correcting a scattered light signal affected by the change of a temperature of skin or tissue is being studied.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

According to an aspect of an exemplary embodiment, there is provided an apparatus configured to estimate biometric information, the apparatus including: a sensor configured to measure a light signal reflected from a subject and a temperature of the subject; and a processor configured to perform temperature correction on the light signal reflected from the subject based on the temperature of the subject using a light signal-temperature relationship between the light signal reflected from the subject and the temperature of the subject to thereby obtain a temperature-corrected light signal, and estimate the biometric information of the subject based on the temperature-corrected light signal.

The processor may be configured to generate the light signal-temperature relationship in advance in a reference state.

The reference state may include a fasting state of the subject.

The sensor may include a light source configured to emit the light signal to the subject, a light sensor configured to measure the light signal by detecting the light signal reflected from the subject, and a temperature sensor configured to measure the temperature of the subject.

The sensor may include a plurality of light sensors and a plurality of temperature sensors, each of the temperature sensors being provided in proximity to a corresponding light sensor of the plurality of light sensors.

The processor may be configured to generate the light signal-temperature relationship based on light signals measured by each of the plurality of light sensors and temperatures measured by each of the plurality of temperature sensors corresponding to the respective light sensors.

The processor may be configured to select a light sensor to be used for estimating the biometric information from among the plurality of light sensors based on intensities of the light signals measured by each of the plurality of light sensors.

The processor may be configured to perform temperature corrections on the light signals measured by each of the plurality of light sensors using the temperatures measured by each of the temperature sensors corresponding to the respective light sensors, generate temperature-corrected light signals based on the temperature corrections, and select the light sensor to be used for estimating the biometric information from among the plurality of light sensors based on intensities of the temperature-corrected light signals.

The biometric information may include at least one of triglyceride, blood sugar, moisture, hemoglobin, cholesterol, alcohol, and fat.

The apparatus may further include a display configured to display the measured light signal, the measured temperature, or the estimated biometric information.

The apparatus may further include a communicator configured to transmit the measured light signal, the measured temperature, or the estimated biometric information to an external electronic device.

The processor may be configured to make a determination as to whether the measured temperature is abnormal, and according to the determination, request the sensor to re-measure the light signal or the temperature, or correct the light signal-temperature relationship.

According to an aspect of another exemplary embodiment, there is provided a method of estimating biometric information, the method including: measuring a light signal reflected from a subject and a temperature of the subject; performing temperature correction on the light signal reflected from the subject based on the temperature of the subject using a light signal-temperature relationship between the light signal reflected from the subject and the temperature of the subject to thereby obtain a temperature-corrected light signal; and estimating the biometric information of the subject based on the temperature-corrected light signal.

The method may further include generating the light signal-temperature relationship in advance in a reference state.

The reference state may include a fasting state of the subject.

The biometric information may include at least one of triglyceride, blood sugar, moisture, hemoglobin, cholesterol, alcohol, and fat.

The method may further include displaying the measured light signal, the measured temperature, or the estimated biometric information.

According to an aspect of another exemplary embodiment, there is provided an apparatus configured to estimate biometric information, the apparatus including: a sensor configured to measure, at predetermined time intervals, a light signal reflected from a subject and a temperature of the subject in a reference state; and a processor configured to generate a light signal-temperature relationship between the light signal reflected from the subject and the temperature of the subject, by using the light signal reflected from the subject and the temperature of the subject as learning data to generate the light-signal temperature relationship.

The reference state may include a fasting state of the subject.

The sensor may be configured to measure the light signal reflected from the subject and the temperature of the subject during a predetermined time period and the processor may be configured to generate the light signal-temperature relationship based on the light signal reflected from the subject and the temperature of the subject measured during the predetermined time period.

Other exemplary features and aspects will be apparent from the following detailed description, the drawings, and the claims.

BRIEF DESCRIPTION OF THE DRAWINGS

The above and other exemplary aspects and advantages will become apparent and more readily appreciated from the following detailed description of certain exemplary embodiments, taken in conjunction with the accompanying drawings of which.

Figure 1:
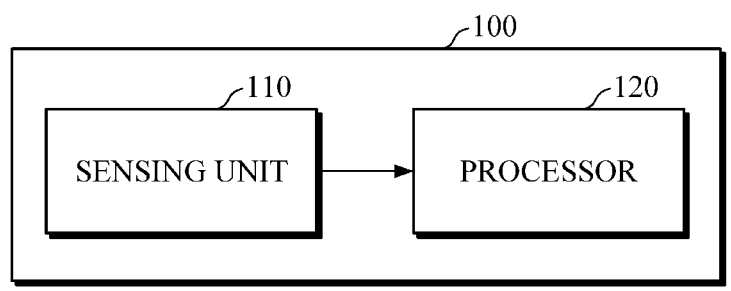
FIG. 1 is a block diagram illustrating an apparatus for estimating biometric information according to an exemplary embodiment.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

Exemplary, non-limiting advantages and features may be understood more readily by reference to the following detailed description of exemplary embodiments and the accompanying drawings. Apparatuses and methods may, however, be embodied in many different forms and should not be construed as being limited to the exemplary embodiments set forth herein. Rather, these exemplary embodiments are provided so that this disclosure will be thorough and complete and will fully convey the concept of the exemplary embodiments to those skilled in the art, and the exemplary embodiments will only be defined by the appended claims. Like reference numerals refer to like elements throughout the specification.

It will be understood that, although the terms first, second, etc., may be used herein to describe various elements, these elements should not be limited by these terms. These terms are only used to distinguish one element from another. Also, the singular forms are intended to include the plural forms as well, unless the context clearly indicates otherwise. In the specification, unless explicitly described to the contrary, the word "comprise" and variations such as "comprises" or "comprising", will be understood to imply the inclusion of stated elements but not the exclusion of any other elements. The term 'unit', as used herein, may refer to, but is not limited to referring to, a software or hardware component, such as a Field Programmable Gate Array (FPGA) or Application Specific Integrated Circuit (ASIC), which performs certain tasks. A unit may advantageously be configured to reside on the addressable storage medium and configured to execute on one or more processors.

Thus, a unit may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The functionality provided for in the components and units may be combined into fewer components and units or further separated into additional components and units.

FIG. 1 is a block diagram illustrating an apparatus for estimating biometric information according to an exemplary embodiment.

Referring to FIG. 1, the apparatus 100 for estimating biometric information includes a sensing unit 110 (e.g., sensor) and a processor 120.

The sensing unit 110 may measure a light signal reflected from a subject and measure a temperature of the subject in order to generate a light signal-temperature relationship. In this case, the light signal reflected from the subject may include a scattered light signal that is specularly reflected from the surface of the subject and a scattered light signal that is diffuse and is reflected from an inside of the irradiated subject. When a user's command is input to the apparatus 100 or when the apparatus 100 is in a reference state, the sensing unit 110 may measure the light signal and/or temperature from the subject. For example, the user's command may be input to the apparatus 100 through a standard input device, such as a keyboard, a mouse, or a voice processor, which is mounted in or connected to the apparatus 100. In this case, the reference state may include a fasting state of the subject and may be set differently according to an age, sex and/or skin condition of the user and/or according to the biometric information to be measured.

Data about the light signal and/or temperature measured by the sensing unit 110 may be stored in a database disposed inside and/or outside of the apparatus 100. The database may store the data about the light signal and/or temperature by matching it with the user, measurement time, and the like. For example, the database may include a solid state drive and a hard disk drive, and the hard disk drive may include a buffer 1, a hard disk drive (HDD) controller, a driver, a read/write (R/W) channel circuit, and a head disk assembly (HAD).

The processor 120 may perform temperature correction by applying the temperature measured from the subject to the light signal measured from the subject using the light signal-temperature relationship. More specifically, the processor 120 may perform temperature correction on the basis of the light signal-temperature relationship by subtracting or excluding a signal or a portion of a signal associated with the temperature from the light signal measured the subject.

In the reference state, the processor 120 may generate the light signal-temperature relationship in advance. In addition, in order to generate in advance the light signal-temperature relationship in the reference state, the sensing unit 110 may measure the light signal and/or temperature from the subject in the reference state.

Referring to Equation 1 below, it is seen that a scattered light signal $X_{scattered\ light}$ (a scattered light signal reflected from the subject) is the same as or proportional to a value obtained by adding a signal $X_{biological}$ generated by the biometric information of the subject, a signal $X_{temperature}$ generated by temperature, and an error value $X_{error}$. However, for convenience of description, it will be assumed that $\Delta X_{error}$ is zero.

$$\Delta X_{scattered\ light} \cong \Delta X_{biological} + \Delta X_{temperature} + \Delta X_{error} \quad \text{Equation (1)}$$

If $\Delta X_{biological}$ is zero or is small enough to be assumed zero, as shown in Equation 2 below, Equation 1 may be expressed as Equation 2. For example, in the case where there is no change of substance in the blood of the subject, the following Equation 2 may be applied when the light signal and temperature are measured from the subject.

$$\Delta X_{scattered\ light} \cong \Delta X_{temperature}(\text{if}, \Delta X_{biological} \cong 0) \quad \text{Equation (2)}$$

That is, the processor 120 assumes that the light signal $X_{scattered\ light}$ that is measured when $\Delta X_{biological}$ is zero or small enough to be assumed zero is a signal $X_{temperature}$ which is generated by temperature, and may generate the light signal-temperature relation on the basis of the relationship between the temperature at the time of light signal measurement and the light signal $X_{scattered\ light}$.

Meanwhile, when triglyceride or blood sugar of the subject is considered as biometric information, the above Equation 1 may be expressed as Equation 3 below. (In Equation 3, $\Delta X_{triglyceride}$ (triglyceride) is stated, but it may be replaced by $\Delta X_{blood\ sugar}$ (blood sugar)).

$$\Delta X_{scattered\ light} \cong \Delta X_{triglyceride} + \Delta X_{temperature} + \Delta X_{error} \quad \text{Equation (3)}$$

Meanwhile, when the subject is in a fasting state, $\Delta X_{triglyceride}$ or $\Delta X_{blood\ sugar}$) is zero or small enough to be assumed zero, and thus the above Equation 3 for the subject in a fasting state may be expressed as the following Equation 4.

$$\Delta X_{scattered\ light} \cong \Delta X_{temperature}(\text{subject is in a fasting state}) \quad \text{Equation (4)}$$

Therefore, the processor 120 may generate the light signal-temperature relation on the basis of the relationship between the scattered light signal measured in a fasting state of the subject and the temperature at the time of measuring the scattered light signal.

Meanwhile, the processor 120 may generate the light signal-temperature relationship in advance before extracting the biometric information. In addition, the light signal-temperature relation generated in advance by the processor 120 may be stored in the database, wherein the light signal-temperature relation may be matched with the measurement time, the measured light signal and/or temperature.

Additionally, the processor 120 may determine whether the measured temperature is abnormal, and may request the sensing unit 110 to re-measure a light signal and/or temperature or correct the light signal-temperature relationship in consideration of the measured temperature according to the determination. For example, when the temperature measured at the time of measuring the light signal from the subject for generating the light signal-temperature relation deviates from a predetermined temperature range (e.g., a room temperature, 15° C. to 20° C.), the processor 120 may determine that the measured temperature is abnormal. In addition, the processor 120 may repeatedly request the sensing unit 110 to re-measure the light signal and/or temperature until the temperature measured from the subject is within the predetermined temperature range. Meanwhile, the processor 120 may correct the light signal-temperature relationship by taking into consideration a degree of deviation (difference) of the measured temperature from the predetermined temperature range.

In one example, when the user of the apparatus 100 measures a light signal and/or temperature from the subject in order to generate a light signal-temperature relationship for ultra-low temperature environments, such as a refrigerated cold storage warehouse, an ultra-high altitude region, the Antarctic area, and the like, the generated light signal-temperature relation is difficult to be applied to a general environment. Therefore, the processor 120 may request the sensing unit 110 to measure the light signal and/or temperature when the apparatus 100 is in a general environment or may correct the light signal-temperature relationship in consideration of the fact that the light signal-temperature relationship has been generated for the ultra-low temperature environments.

The processor 120 may estimate the biometric information of the subject on the basis of a temperature-corrected light signal. In this case, the biometric information may include a substance contained in the body of the subject, including triglyceride, blood sugar, moisture, hemoglobin, cholesterol, alcohol, fat, and the like. The processor 120 may calculate a scattering coefficient from the temperature-corrected light signal, and estimate the biometric information of the subject on the basis of the calculated scattering coefficient. For example, the processor 120 may estimate triglyceride content or blood sugar level of the subject on the basis of the temperature-corrected light signal. In another example, the processor 120 may estimate triglyceride content or blood sugar level of the subject on the basis of a light signal which is not temperature-corrected.

In addition, the processor 120 may determine the health status of the subject on the basis of the estimated biometric information. For example, the processor 120 may compare the estimated triglyceride content and/or blood sugar level of the subject with a predetermined reference value and determine whether the subject's health status is abnormal. In addition, the processor 120 may compare the estimated triglyceride content and/or blood sugar level with a predetermined reference value and determine a degree of risk of a disease associated with the triglyceride content and/or blood sugar level of the subject according to a degree to which a difference between the compared values deviates from a predetermined tolerance range. For example, the processor 120 may determine that the greater the difference between the triglyceride content and/or blood sugar level and the reference value is, the higher the risk of a disease associated with the triglyceride content and/or blood sugar level of the subject is.

The processor 120 may include a bus and a predetermined electronic circuit (or an integrated circuit). The processor 120 may realize various functions to be implemented in the apparatus 100 for estimating biometric information and control and manage the overall operation of the apparatus 100 in order to realize the functions described below.

Figure 2:
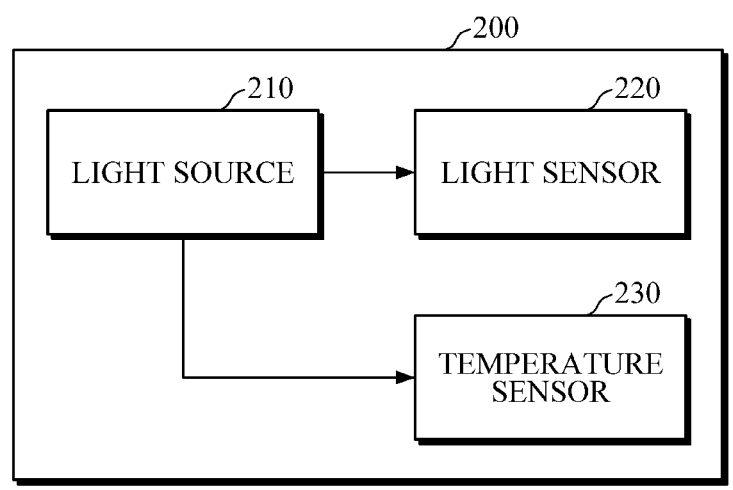
FIG. 2 is a block diagram illustrating a sensing unit according to an exemplary embodiment.

FIG. 2 is a block diagram illustrating a sensing unit according to an exemplary embodiment.

Referring to FIG. 2, the sensing unit 200 includes a light source 210, a light sensor 220, and a temperature sensor 230.

The light source 210 may emit light to a subject. For example, the light source 210 may include a light emitting diode. Here, the light emitting diode may be a light emitting device which emits light, such as RGB light, RGBW light, infrared light, near-infrared light, mid-infrared light, and the like. In addition, the light source 210 may include a fixing device to fix the light emitting diode so as to emit light to the subject at a predetermined angle or an angle adjusting device to adjust the angle at which the light emitting diode emits light to the subject in response to a control signal of the processor 120. In addition, the light source 210 may include one or more light source modules configured as independent modules, and each light source module may be set to emit light of a different wavelength band or set to sequentially and repeatedly emit light of multiple wavelength bands.

When the emitted light is reflected from the subject, the light sensor 220 may measure a light signal by detecting the reflected light. For example, the light sensor 220 may include a photodiode, a photo transistor (PTr), or a charge-coupled device (CCD), but is not limited thereto. The light sensor 220 may detect a light signal from at least one of light reflected from the skin of the subject which is transmitted by the light source, absorption light, and light scattered by a biological component. In addition, one or more light sensors 220 may be provided and be implemented as an array of a predetermined structure spaced apart from the light source 210 at a specific distance.

The temperature sensor 230 may measure a temperature of the subject. For example, the temperature sensor 230 may include an infrared temperature sensor which measures the temperature of the subject by detecting infrared rays (e.g., thermal infrared rays, mid-infrared rays, near infrared rays) radiated from the subject.

In addition, the light source 210 may include one or more light source modules, and the processor 120 may determine an optimal light source module for estimating biometric information on the basis of the light signal detected by the light sensor 220. For example, the optimal light source module for estimating biometric information may vary depending on the positions of the light source 210 and the light sensor 220, wherein the optimal light source may refer to a light source module disposed at a specific position among one or more light source modules included in the light source 210. However, aspects of the exemplary embodiments are not limited to those described above, and in the case where the light source 210 includes one or more modules each of which is set to emit light of a specific wavelength band, the optimal light source may refer to a light source module which emits light of a particular wavelength band.

Figure 3:
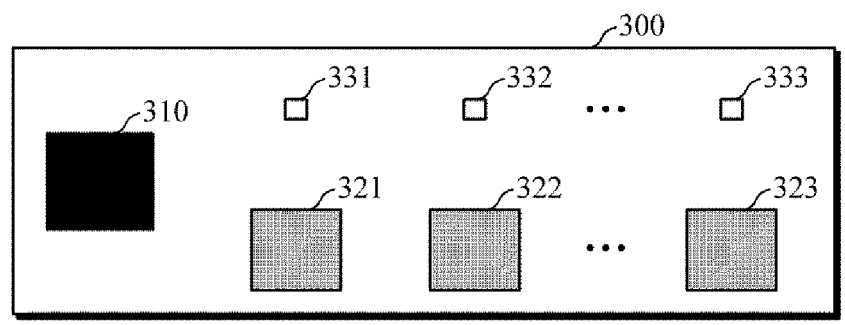
FIG. 3 is a diagram illustrating a sensing unit according to an exemplary embodiment.

FIG. 3 is a diagram illustrating a sensing unit according to an exemplary embodiment.

Referring to FIG. 3, the sensing unit 300 includes a light source 310, a plurality of light sensors 321, 322, and 323, and a plurality of temperature sensors 331, 332, and 333, and each of the temperature sensors 331 to 333 may be disposed in proximity to one of the plurality of light sensors 321 to 323. That is, as shown in FIG. 3, the first temperature sensor 331 is disposed close to the first light sensor 321, the second temperature sensor 332 is disposed close to the second light sensor 322, and the third temperature sensor 333 is disposed close to the third light sensor 323. Although FIG. 3 shows only three light sensors 321 to 323 and three temperature sensors 331 to 333, these sensors are only illustrated to represent all of the plurality of light sensors 321 to 323 and the plurality of temperature sensors 331 to 333 in one drawing, and the number of light sensors 321 to 323 and the number of temperature sensors 331 to 333 are each not limited to three as shown in FIG. 3. In addition, although FIG. 3 illustrates an example in which the number of light sensors 321 to 323 is the same as the number of temperature sensors 331 to 333, the number of light sensors 321 to 323 and the number of temperature sensors 331 to 333 may be different from each other.

The processor 120 may generate a light signal-temperature relationship which corresponds to each of the light sensors 321 to 323. Referring to FIG. 3, the sensing unit 300 includes three light sensors 321 to 323 and three temperature sensors 321 to 323, and thus the processor 120 may generate the first light signal-temperature relationship (Equation 5, below) on the basis of a relationship between a temperature and a light signal measured by the first temperature sensor 331 and the first light sensor 321, the second light signal-temperature relationship (Equation 6, below) on the basis of a relationship between a temperature and a light signal measured by the second temperature sensor 332 and the second light sensor 322, and the third light signal-temperature relationship (Equation 7, below) on the basis of a relationship between a temperature and a light signal measured by the third temperature sensor 333 and the third light sensor 323.

$$Y_{first\ light\ sensor} = a_1 * X_{first\ temperature\ sensor} + b_1 \quad \text{Equation (5)}$$

$$Y_{second\ light\ sensor} = a_2 * X_{second\ temperature\ sensor} + b_2 \quad \text{Equation (6)}$$

$$Y_{third\ light\ sensor} = a_3 * X_{third\ temperature\ sensor} + b_3 \quad \text{Equation (7)}$$

However, Equations 5 to 7 are only examples to show the light signal-temperature relationships as linear relationships. In addition, the light signal-temperature relations may not be linear relationships, unlike Equations 5 to 7.

The processor 120 may generate or correct the light signal-temperature relationship on the basis of the light signals and/or temperatures which are measured a number of times by the plurality of light sensors 321 to 323 and the plurality of temperature sensors 331 to 333, respectively, in order to increase the accuracy of the light signal-temperature relationship.

In another example, the processor 120 may request the plurality of light sensors 321 to 323 and temperature sensors 331 to 333 to measure the light signal and/or temperature several times, and may generate the light signal-temperature relationship on the basis of maximum values of a plurality of light signals and/or temperatures measured, an average of the maximum values, minimum values, an average of the minimum values, and an intermediate value between the maximum value and the minimum value.

In another example, the processor 120 may request the plurality of light sensors 321 to 323 and temperature sensors 331 to 333 to measure the light signal and/or temperature several times, and may correct a light signal-temperature relationship previously generated by learning a plurality of light signals and/or temperatures measured by the plurality of light sensors 321 to 323 and temperature sensors 331 to 333. For example, the processor 120 may use a deep-learning algorithm, such as long short-term memory (LSTM), deep neural network (DNN), recurrent neural network (RNN), bidirectional recurrent deep neural network (BRDNN), convolutional neural network (CNN), restricted Boltzmann machine (RBM), deep belief network (DBN), and the like, when learning the plurality of light signals and/or temperatures measured by the plurality of light sensors 321 to 323 and temperature sensors 331 to 333.

The processor 120 may select a light sensor to be used for estimating biometric information from among the plurality of light sensors 321 to 323.

For example, the processor 120 may use all of the plurality of light sensors 321 to 323 when measuring a light signal from the subject in order to generate the light signal-temperature relationship. Also, in the case where the processor 120 measures the light signal from the subject in order to estimate biometric information, the processor 120 may select some light sensors from among the plurality of light sensors 321 to 323 according to a predetermined criterion.

For example, the processor 120 may select a light sensor to be used for estimating biometric information by taking into consideration the signal intensity of the measured light signal, wherein the processor 120 may select the light signal from among the light signals measured by the plurality of light sensors 321 to 323 according to the order of intensities of the light signals and select the light sensor that corresponds to the selected light signal as the light sensor to be used for estimating biometric information.

In another example, the processor 120 may calculate a signal-to-noise (SNR) of a light signal detected by each of the light sensors 321 to 323 and select the light sensor that detects a light signal having the highest SNR among the calculated light signals as the light sensor used for estimating biometric information.

The processor 120 may correct temperatures of the light signals measured by the plurality of light sensors 321 to 323 and select a light sensor to be used for estimating biometric information from among the temperature-corrected light sensors 321 to 323.

For example, the processor 120 may select the light sensor to be used for estimating biometric information by taking into consideration signal intensities of the temperature-corrected light signals, wherein the processor 120 may select the light sensor to be used for estimating biometric information in the order of highest intensity to weakest intensity of the temperature-corrected light signal.

In another example, the processor 120 may select a light sensor to be used for estimating biometric information on the basis of a light signal which is not temperature corrected.

The processor 120 may extract biometric information of the subject, as described above.

More specifically, the processor 120 may calculate a triglyceride content using the following Equation 8 on the basis of an intensity of a scattered light detected by the sensing unit 110. Hereinafter, in the description related to Equation 8, it is assumed that two light sensors are selected from the plurality of light sensors according to various criteria described above.

$$\mu_s' = \frac{1}{3\mu_a}\left\{\frac{1}{\rho_2 - \rho_1}\ln\frac{\rho_1^2 R_1(\rho_1)}{\rho_2^2 R_2(\rho_2)}\right\} \quad \text{Equation (8)}$$

Here, $\mu_s'$ may denote a reduced scattering coefficient, $\mu_a$ may denote an absorption coefficient, $\rho_1$ may denote a distance from the light source 310 to the first light sensor 331, $\rho_2$ may denote a distance from the light source 310 to the second light sensor 322, $R_1$ may denote the intensity of a scattered light at the first light sensor 331, and $R_2$ may denote the intensity of a scattered light at the second light sensor 332. The processor 120 may calculate an amount of change in the reduced scattering coefficient, which may be defined as a ratio $R_1/R_2$ of intensities of two detected scattered light signals, and may measure the triglyceride content of the subject. For example, the processor 120 may calculate the reduced scattering coefficient in a reference state (e.g., a fasting state of the subject), in which the triglyceride content of the subject does not change, calculate the reduced scattering coefficient after a predetermined amount of time has elapsed since consumption of food containing fat, and compute an amount of change in the reduced scattering coefficient, thereby calculating the triglyceride content of the subject.

According to another exemplary embodiment, the sensing unit 300 may include a plurality of light sensors 220 and one temperature sensor 230. For example, the temperature sensor 230 may be disposed in proximity to one of light sensors 220, or may be disposed at a position which is equally spaced apart from each of the light sensors 220.

In addition, in the sensing unit 300, each of the light sensors 220 may measure a light signal and the single temperature sensor 230 may measure a temperature of the subject. Meanwhile, the processor 120 may generate as many light signal-temperature relationships as the number of light sensors 220 on the basis of relationships between each of the light signals measured by the respective light sensors 220 and the temperature measured by the temperature sensor 230.

More specifically, in a case where the sensing unit 300 includes three light sensors 220 and one temperature sensor 230, the processor 120 may generate the first light signal-temperature relationship (Equation 9, below) on the basis of a relationship between a light signal measured by the first light sensor and a temperature measured by the temperature sensor, the second light signal-temperature relationship (Equation 10, below) on the basis of a relationship between a light signal measured by the second light sensor and the temperature measured by the temperature sensor, and the third light signal-temperature relationship (Equation 11, below) on the basis of a relationship between a light signal measured by the third light sensor and the temperature measured by the temperature sensor.

$$Y_{\text{first light sensor}} = c_1 * X_{\text{temperature sensor}} + d_1 \quad \text{Equation (9)}$$

$$Y_{\text{second light sensor}} = c_2 * X_{\text{temperature sensor}} + d_2 \quad \text{Equation (10)}$$

$$Y_{\text{third light sensor}} = c_3 * X_{\text{temperature sensor}} + d_3 \quad \text{Equation (11)}$$

However, Equations 9 to 11 are merely examples which illustrate the light signal-temperature relationships as linear relationships. In addition, the light signal-temperature relationships may not be linear relationships, unlike Equations 8 to 10.

Figure 4:
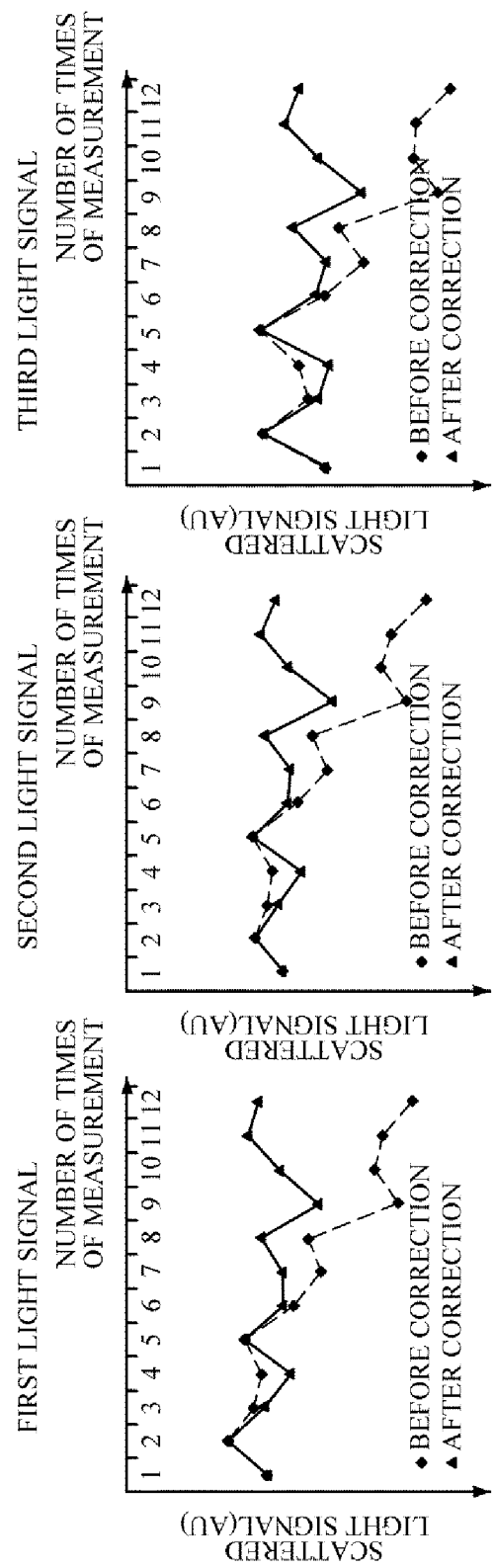
FIG. 4 illustrates graphs for describing a result of performing temperature correction on a scattered light signal.

FIG. 4 show graphs for describing a result of performing temperature correction on a scattered light signal.

FIG. 4 illustrates light signals measured by each of three light sensors 331 to 333 of the sensing unit 300 and temperature-corrected light signals.

Referring to FIG. 4, it is shown that a value of the scattered light signal increases as the number of times of measurement increases. This results from the fact that the signal generated by the temperature increases as the number of times of measurement increases. As the number of times of measurement increases or as the elapsed time of operation of the apparatus 100 for estimating biometric information increases, the heat generated by the apparatus 100 increases, and accordingly the magnitude of the signal generated by the temperature may gradually increase.

Referring to the light signals after temperature correction, it is shown that the signals generated by the temperature are excluded.

Figure 5:
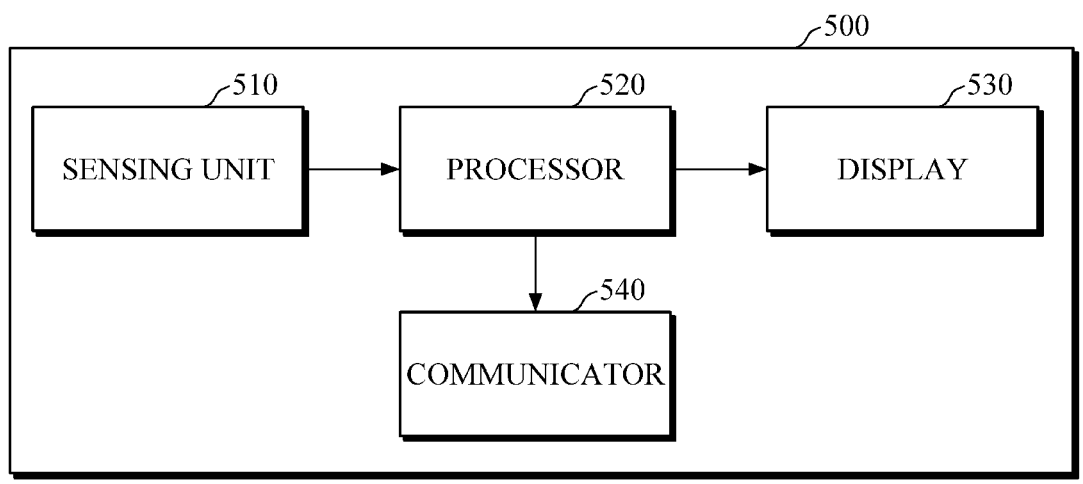
FIG. 5 is a block diagram illustrating an apparatus for estimating biometric information according to another exemplary embodiment.

FIG. 5 is a block diagram illustrating an apparatus for estimating biometric information according to another exemplary embodiment.

Referring to FIG. 5, the apparatus 500 for estimating biometric information includes a sensing unit 510 (e.g., sensor), a processor 520, a display 530, and a communicator 540. The sensing unit 510 and the processor 520 have been described above in detail with reference to FIG. 1, and hence a redundant or unnecessary description will be omitted herein.

The display 530 may display a light signal or temperature measured at the sensing unit 510 or biometric information estimated by the processor 520. For example, the display 530 may display a triglyceride content or blood sugar level estimated by the processor 520 on the basis of the light signal and temperature measured at the sensing unit 510. In addition, the display 530 may display a graph to show changes in triglyceride content or blood sugar level over time, and the apparatus 500 may be utilized as a monitoring device to monitor the health status of the subject.

The processor 520 may monitor the trend of changes in biometric information of the subject during a predetermined period of time. For example, the processor 520 may obtain a maximum value or minimum value of each of the graphs generated at predetermined intervals and may detect a trend of changes in maximum value or minimum value on the basis of a rise or fall of the obtained value. However, since the rise or fall of the maximum value or minimum value of the biometric information may temporarily appear, the processor 520 may determine that the biometric information of the subject is rising or falling when the rise or fall of the maximum value or minimum value continues beyond a predetermined reference period.

In addition, the display 530 may generate a user interface screen for displaying at least one piece of specific information arranged in chronological order along one axis. More specifically, the display 530 may generate the user interface screen for arranging pieces of information contained in health-related information in chronological order and displaying the arranged information in a horizontal direction or a vertical direction.

The communicator 540 may transmit the light signal or temperature measured by the sensing unit 510 or the estimated biometric information to an external electronic device. For example, the communicator 540 may communicate with the external electronic device through a wireless or wired communication. Here, the wireless communication may include Bluetooth communication, Bluetooth low energy (BLE) communication, near field communication (NFC), wireless local area network (WLAN) communication, ZigBee communication, infrared data association (IrDA) communication, Wi-Fi direct (WFD) communication, ultra-wideband (UWB) communication, Ant+ communication, Wi-Fi communication, radio frequency identification (RFID) communication, 3G communication, 4G communication, 5G communication, or the like. Also, the wired communication may include a universal serial bus (USB), high definition multimedia interface (HDMI), recommended standard 232 (RS-232), a plain old telephone service (POTS), or the like.

Additionally, the apparatus 500 for estimating biometric information may further include an application to provide an application related to biometric information estimation.

For example, the application may include a short message service (SMS) application or a multimedia messaging service (MMS) application, an email application, a calendar application, an alarm application, a healthcare application (e.g., an application for measuring an amount of exercise, a blood sugar level, or the like), an environment information application (e.g., an application for providing atmospheric pressure information, humidity information, or temperature information), or the like.

In addition, the application may be an application related to information exchange between the apparatus 500 and the external electronic device. In this case, the application related to information exchange may include a notification relay application for transmitting specific information to the external electronic device or a device management application for managing the external electronic device.

Also, the application may include a function for transmitting notification information generated in the application (e.g., SMS or MMS application, email application, healthcare application, environment information application or the like.) of the apparatus 500 to the external electronic device. In another example, the application may receive notification information from the external electronic device and provide it to the user. In still another example, the application may manage (e.g., install, delete, or update) at least some functions (e.g., turning on or off of the external electronic device itself or some components thereof or control of brightness or resolution) of the external electronic device, applications running on the external electronic device, or services (e.g., call services or message services) provided by the external electronic device.

Figure 6:
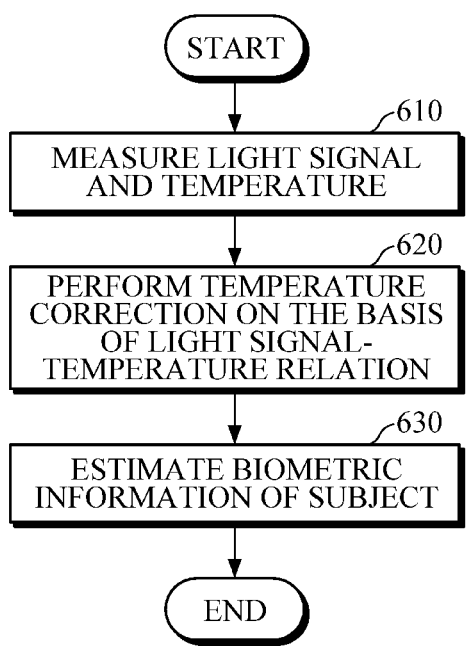
FIG. 6 is a flowchart illustrating a method of estimating biometric information according to an exemplary embodiment.

FIG. 6 is a flowchart illustrating a method of estimating biometric information according to an exemplary embodiment.

Referring to FIG. 6, the apparatus 500 for estimating biometric information measures a light signal reflected from a subject and measures a temperature of the subject in order to generate a light signal-temperature relationship, in operation 610. In this case, the light signal reflected from the subject may include a scattered light signal that is specularly reflected from the surface of the subject and a scattered light signal that is diffuse reflected from the inside of the irradiated subject. For example, the apparatus 500 may measure the light signal and/or temperature of the subject when a user's command is input to the apparatus 500 or the apparatus 500 is in a reference state.

The apparatus 500 performs temperature correction on the light signal measured from the subject with reference to the measured temperature on the basis of the light signal-temperature relationship, in operation 620. More specifically, the apparatus 500 may perform the temperature correction on the basis on the light signal-temperature relationship by subtracting or excluding a signal associated with the temperature from the measured light signal reflected by the subject.

In a reference state, the apparatus 500 may generate the light signal-temperature relationship in advance. In this case, the reference state may include a fasting state of the subject and may be set differently according to the age, sex and skin condition of the user and the biometric information to be measured. In addition, the light signal-temperature relationship generated in advance by the apparatus 500 may be stored in a database, wherein the light signal-temperature relationship may be matched with the measurement time, the measured light signal and/or temperature.

The apparatus 500 estimates biometric information of the subject on the basis of the temperature-corrected light signal, in operation 630. In this case, the biometric information may include at least one of triglyceride, blood sugar, moisture, hemoglobin, cholesterol, alcohol, and fat. Also, the apparatus 500 may calculate a scattering coefficient from the temperature-corrected light signal and estimate the biometric information of the subject on the basis of the extracted scattering coefficient. For example, the apparatus 500 may estimate a triglyceride content or blood sugar level of the subject on the basis of the temperature-corrected light signal. In another example, the apparatus 100 may estimate the triglyceride content or blood sugar level of the subject on the basis of the light signal which is not temperature-corrected.

Additionally, the apparatus 500 for estimating biometric information may display the measured light signal and/or temperature or the estimated biometric information on a display. For example, the apparatus 500 may display the triglyceride content or blood sugar level estimated on the basis of the measured light signal and temperature on the display. In addition, the apparatus 500 may display a graph to show changes in triglyceride content or blood sugar level over time.

The apparatus 500 may monitor the trend of changes in biometric information of the subject during a predetermined period of time. For example, the apparatus 500 may obtain a maximum value or minimum value of each of the graphs generated at predetermined intervals and may detect a trend of changes in maximum value or minimum value on the basis of a rise or fall of the obtained value. However, since the rise or fall of the maximum value or minimum value of the biometric information may temporarily appear, the apparatus 500 may determine that the biometric information of the subject is rising or falling when the rise or fall of the maximum value or minimum value continues beyond a predetermined reference period.

In addition, the apparatus 500 may generate a user interface screen for displaying at least one piece of specific information arranged in chronological order along one axis. More specifically, the apparatus 500 may generate the user interface screen for arranging pieces of information contained in health-related information in chronological order and displaying the arranged information in a horizontal direction or a vertical direction.

Figure 7:
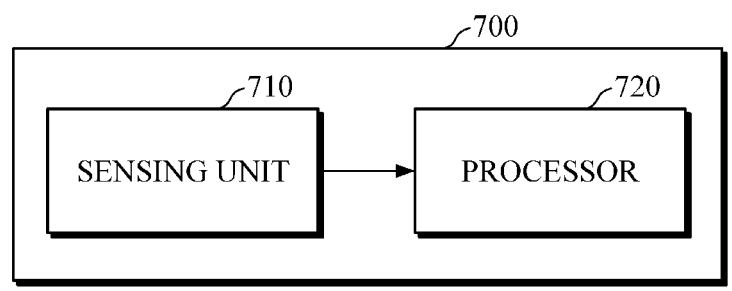
FIG. 7 is a block diagram illustrating an apparatus for estimating biometric information according to another exemplary embodiment.

FIG. 7 is a block diagram illustrating an apparatus for estimating biometric information according to another exemplary embodiment.

Referring to FIG. 7, the apparatus 700 includes a sensing unit 710 (e.g, sensor) and a processor 720.

In a reference state, the sensing unit 710 may measure a light signal and/or temperature from a subject at predetermined time intervals. Here, the predetermined time interval may be set to days, weeks, months, years, etc., but is not limited thereto, and may vary according to the health status of the user or the purpose of biometric information estimation. For example, the light signal and/or temperature may be set to be measured at shorter intervals in the case where the user's health status is poor, and the time interval may be set to a relatively long period in the case where data is to be collected over a long period of time. In addition, the reference state may include a fasting state of the subject and may be set differently according to the age, sex, and skin condition of the user and the type of biometric information to be measured.

The sensing unit 710 may include a light source, a light sensor, and a temperature sensor to measure a light signal and a temperature.

In this case, the light source of the sensing unit 710 may emit light to the subject. For example, the light source may include a light emitting diode to emit light to the subject. Here, the light emitting diode may be a light emitting device which emits light, such as RGB light, RGBW light, infrared light, near-infrared light, mid-infrared light, and the like. The sensing unit 710 may include one or more light source modules configured as independent modules, and each light source module may be set to emit light of a different wavelength band or set to sequentially and repeatedly emit light of multiple wavelength bands.

When the emitted light is reflected from the subject, the light sensor of the sensing unit 710 may measure a light signal by detecting the reflected light. For example, the light sensor of the sensing unit 710 may include a photodiode, a PTr, or a CCD, but is not limited thereto. The light sensor of the sensing unit 710 may detect a light signal from at least one of light reflected from the skin of the subject which is irradiated by the light source, absorption light, and light scattered by a biological component.

The temperature sensor of the sensing unit 710 may measure a temperature of the subject. For example, the temperature sensor of the sensing unit 710 may include an infrared temperature sensor which measures the temperature of the subject by detecting infrared rays (e.g., thermal infrared rays, mid-infrared rays, near infrared rays) radiated from the subject.

The processor 720 may generate a light signal-temperature relationship using the measured light signal and/or temperature as learning data. For example, the apparatus 700 for estimating biometric information may include a database inside or outside thereof to store data on the light signal and/or temperature measured by the sensing unit 710. In addition, the processor 720 may generate a linear equation or a predetermined expression of a relationship which represents a relationship between a light signal and a temperature, on the basis of the light signal and the temperature measured using the sensing unit 710 in the reference state.

The sensing unit 710 may measure a light signal and a temperature at a predetermined time period, and the processor 720 may generate the light signal-temperature relationship on the basis of the light signal and temperature measured at the predetermined time period.

For example, the user of the apparatus 700 may set a time period during which it is determined that a fasting state is periodically maintained. If the predetermined time period is from 6 a.m. to 7 a.m., the sensing unit 710 may measure a light signal or a temperature from the subject at predetermined time intervals (e.g., 10 minutes, 15 minutes, etc.). The processor 720 may generate the light signal-temperature relationship on the basis of the light signal and/or temperature measured at the predetermined time period, and the light signal-temperature relationship may be assumed as a light signal-temperature relatiionship generated on the basis of the light signal and/or temperature measured in the reference state.

Figure 8:
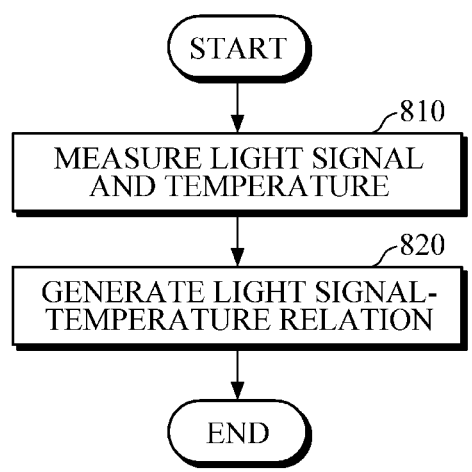
FIG. 8 is a flowchart illustrating a method of estimating biometric information according to another exemplary embodiment.

FIG. 8 is a flowchart illustrating a method of estimating biometric information according to another exemplary embodiment.

Referring to FIG. 8, the apparatus 700 for estimating biometric information may measure a light signal and/or temperature from a subject in a fasting state at a predetermined time interval, in operation 810. Here, the predetermined time interval may be set to days, weeks, months, years, etc., but is not limited thereto, and may vary according to the health status of the user or the purpose of biometric information estimation. In addition, the reference state may include a fasting state of the subject and may be set differently according to the age, sex, and skin condition of the user and the type of biometric information to be measured. The apparatus 700 may store the measured light signal and/or temperature as learning data.

The apparatus 700 generates a light signal-temperature relationship using the measured light signal and/or temperature as learning data, in operation 820. The apparatus 700 may generate a linear equation or a predetermined expression of a relationship which represents a relationship between a light signal and a temperature, on the basis of the light signal and the temperature measured in the reference state.

The exemplary embodiments can be implemented as computer readable codes in a computer readable record medium. Codes and code segments constituting the computer program can be easily inferred by a skilled computer programmer in the art. The computer readable record medium includes all types of recording media in which computer readable data are stored. Examples of the computer readable recording medium include a ROM, a RAM, a CD-ROM, a magnetic tape, a floppy disk, and an optical data storage. Further, the recording medium may be implemented in the form of a carrier wave such as Internet transmission. In addition, the computer readable recording medium may be distributed to computer systems over a network, in which computer readable codes may be stored and executed in a distributed manner.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus configured to estimate biometric information, the apparatus comprising:
   a sensor configured to measure a first light signal reflected from a subject and a first temperature of the subject while the subject is in a fasting state, and measure a second light signal reflected from the subject and a second temperature of the subject while the subject is in a non-fasting state; and
   a processor configured to generate a light signal-temperature relationship between the first light reflected from the subject and the first temperature of the subject measured in the fasting state, perform temperature correction on the second light signal reflected from the subject based on the second temperature of the subject and the light signal-temperature relationship to thereby obtain a temperature-corrected light signal, and estimate the biometric information of the subject based on the temperature-corrected light signal.

2. The apparatus of claim 1, wherein, when a type of the biometric information is triglyceride or blood sugar, the light signal-temperature relationship indicates that the first light signal measured in the fasting state is a temperature signal generated by heat of the subject corresponding to the first temperature, and perform the temperature correction on the second light signal by removing the temperature signal from the second light signal.

3. The apparatus of claim 1, wherein the sensor comprises a light source configured to emit the first light signal and the second light signal to the subject, a light sensor configured to measure the first light signal and the second light signal by detecting the first light signal and the second light signal reflected from the subject, respectively, and a temperature sensor configured to measure the first temperature and the second temperature of the subject.

4. The apparatus of claim 3, wherein the sensor comprises a plurality of light sensors and a plurality of temperature sensors, each of the temperature sensors being provided in proximity to a corresponding light sensor of the plurality of light sensors.

5. The apparatus of claim 4, wherein the processor is configured to generate the light signal-temperature relationship based on light signals measured by each of the plurality of light sensors and temperatures measured by each of the plurality of temperature sensors corresponding to the respective light sensors.

6. The apparatus of claim 4, wherein the processor is configured to select a light sensor to be used for estimating the biometric information from among the plurality of light sensors based on intensities of the light signals measured by each of the plurality of light sensors.

7. The apparatus of claim 6, wherein the processor is configured to perform temperature corrections on the light signals measured by each of the plurality of light sensors using the temperatures measured by each of the temperature sensors corresponding to the respective light sensors, generate temperature-corrected light signals based on the temperature corrections, and select the light sensor to be used for estimating the biometric information from among the plurality of light sensors based on intensities of the temperature-corrected light signals.

8. The apparatus of claim 1, wherein the biometric information comprises at least one of triglyceride, blood sugar, moisture, hemoglobin, cholesterol, alcohol, and fat.

9. The apparatus of claim 1, further comprising a display configured to display the measured second light signal, the measured second temperature, or the estimated biometric information.

10. The apparatus of claim 1, wherein the processor is configured to determine whether the measured second temperature is within a predetermined temperature range, and correct the light signal-temperature relationship based on a difference between the measured second temperature and the predetermined temperature range in response to the measured second temperature is outside the predetermined temperature range.

11. The apparatus of claim 1, wherein the processor is configured to make a determination as to whether the measured second temperature is within a predetermined temperature range, and repeatedly requests the sensor to re-measure the second light signal and the second temperature until the measured second temperature is within the predetermined temperature range.

12. A method of estimating biometric information, the method comprising:

measuring a first light signal reflected from a subject and a first temperature of the subject while the subject is in a fasting state;

generating a light signal-temperature relationship based on the first light signal reflected from the subject and the first temperature of the subject measured in the fasting state;

measuring a second light signal reflected from the subject and a second temperature of the subject in a non-fasting state;

performing temperature correction on the second light signal reflected from the subject based on the second temperature of the subject and the light signal-temperature relationship to thereby obtain a temperature-corrected light signal; and estimating the biometric information of the subject based on the temperature-corrected light signal.

13. The method of claim 12, wherein:

when a type of the biometric information is triglyceride or blood sugar, the light signal-temperature relationship indicates that the first light signal measured in the fasting state is a temperature signal generated by heat of the subject corresponding to the first temperature, and the performing the temperature correction comprises performing the temperature correction on the second light signal by removing the temperature signal from the second light signal.

14. The method of claim 12, wherein the biometric information comprises at least one of triglyceride, blood sugar, moisture, hemoglobin, cholesterol, alcohol, and fat.

15. The method of claim 12, further comprising displaying the measured second light signal, the measured second temperature, or the estimated biometric information.

16. The apparatus of claim 1, wherein the sensor is further configured to measure the first light signal and the first temperature at predetermined time intervals.

* * * * *